United States Patent [19]

Eikelboom et al.

[11] Patent Number: 4,655,972
[45] Date of Patent: Apr. 7, 1987

[54] CATALYTIC PREPARATION OF CARBONAMIDES

[75] Inventors: Teunis Eikelboom; John A. Rand, both of Gouda; Pieter M. van Dijk, Schoonhoven, all of Netherlands

[73] Assignee: Internationale Octrooi Maatschappij "Octropa" B.V., Rotterdam, Netherlands

[21] Appl. No.: 627,616

[22] Filed: Jul. 3, 1984

[30] Foreign Application Priority Data

Jul. 4, 1983 [NL] Netherlands .......................... 8302367
Jul. 18, 1983 [NL] Netherlands .......................... 8302561

[51] Int. Cl.$^4$ ......................................... C07C 103/133
[52] U.S. Cl. ................................... 260/404; 564/138; 564/139; 564/141; 564/143
[58] Field of Search ................. 260/404; 564/141, 143, 564/139, 138

[56] References Cited

U.S. PATENT DOCUMENTS

| | | | |
|---|---|---|---|
| 2,070,991 | 2/1937 | Hund et al. | 260/404 |
| 3,801,610 | 4/1974 | Werdehausen et al. | 260/404 |
| 3,816,483 | 6/1974 | Werdehausen et al. | 260/404 |
| 3,920,523 | 11/1975 | Lichtenwalter et al. | 260/404 |
| 4,277,410 | 7/1981 | Li et al. | 564/141 |

FOREIGN PATENT DOCUMENTS

| | | | |
|---|---|---|---|
| 2015840 | 10/1970 | Fed. Rep. of Germany | 564/141 |
| 894720 | 4/1962 | United Kingdom | 260/404 |

*Primary Examiner*—Natalie Trousof
*Assistant Examiner*—Bruce D. Gray
*Attorney, Agent, or Firm*—Cushman, Darby & Cushman

[57] ABSTRACT

Carbonamides are prepared from carboxylic acids and ammonia in the presence of a catalytic amount of a hydrated oxide.

Preferably a hydrated titanium-, zirconium- or tin oxide in an amount between 0.05 to 10% by weight is used. The hydrated oxide contains at least 4% of water.

10 Claims, No Drawings

CATALYTIC PREPARATION OF CARBONAMIDES

The application relates to a process for the catalytic preparation of carbonamides starting from carboxylic acid and ammonia at high temperature and possibly elevated pressure under catalytic influence of a metallic compound.

Similar processes are already known from Dutch patent specification No. 171,156 as well as from British patent specification No. 1,396,615. In both documents an organometallic compound is used which is soluble in the reaction mixture and in amounts of 0.1 to 10% by weight based on the reaction mixture.

There are certain drawbacks adhering to the use of a soluble organometallic catalyst. For example, after termination of the conversion it is necessary to convert the organometallic compound chemically and to remove it, e.g. by converting it into an insoluble metallic compound and filtering this off. Consequently there is at least one extra process step necessary and also, moreover, the catalyst can only be used once.

The use of dehydrated $TiO_2$ as a catalyst in the preparation of certain carbonamides is also known from GB-A No. 421 718 and DE-C No. 511 885.

According to the present invention carbonamide is prepared by converting carboxylic acid and ammonia in the presence of a catalytic amount of a hydrated oxide, insoluble in the reaction mixture, of a metal of Group IVa, IVb or Va of the Periodic Table. Preferably the metal has an atomic number below 74. Preferred metallic compounds are hydrated oxides. Especially oxides and hydrated oxides of titanium, zirconium and tin are excellent catalysts.

They are practically insoluble in the reaction mixture (the solubility is as a rule less than about 15 parts per million of the metal involved, which is the detection threshold of the analysis technique followed). The use of these insoluble metallic catalysts has the advantage that their removal is very simple, e.g. by filtration. Also, the repeated use of the catalyst for this reaction is possible and the reaction can, for example, be carried out continuously in a solid bed, which is also a great advantage in process terms.

Other insoluble catalysts for this conversion of carboxylic acid and ammonia were already known, such as various silicates. These, however, are less active than the catalysts derived from metals of the Groups IV and Va.

According to the present invention the hydrated metallic oxide preferably used is hydrated dioxide, more preferably hydrated zirconium and/or titanium dioxide. "Hydrated oxide" means in this connection an oxide containing more than 4%, preferably more than 70% by weight of water. Usually the amount of water is appreciably higher, viz. between 75 and 90% of the weight of the hydrated oxide. The use of more than 95% of water is not recommended. During the reaction some water will also escape from the hydrated metallic oxide and there is water of reaction formed. Sometimes it is advantageous to use the metallic oxide catalyst precipitated on a carrier (e.g. Dicalite). (By "Dicalite" is meant here the product "Perlite" of Grefco Inc., Los Angeles, U.S.A., which is a sodium potassium aluminosilicate of volcanic origin that has been calcined.)

Preferably the hydrated titanium dioxide $(TiO_2).xH_2O$ consists predominantly of orthotitanic acid. More particularly, precipitated hydrated zirconium and/or titanium dioxide is preferably used, such as that can be formed by conversion of the tetrachloride or another (in)organic zirconium or titanium compound with aqueous ammonia.

Examples 2B and 2C show that titanium dioxide in rutile or anatase form is ineffective as catalyst for preparation of carbonamides. Example 3 shows that drying of precipitated, hydrated titanium dioxide very much reduces its catalytic activity.

It is possible to *partially* dry the precipitate without loss of catalytic activity, but in this form the catalyst is more difficult to disperse and charge to either a batch autoclave or a catalyst bed. Moreover, the undried precipitate is easily dispersed, e.g. in a carboxylic acid, and may be easily charged to the reaction vessel. The water can be conveniently and economically removed with the water of reaction. Thus, the preferred form of catalyst is undried, hydrated oxide of a metal of Group IV or VA of the Periodic Table.

The amount of metallic compound which is used can vary within broad limits, depending on the step of the process. For single use the amount is mostly between 0.05 and 10%, preferably between 0.1 and 1.5% by weight, but for re-use and continuous processes it can be considerably higher. The total amount of carbonamide which is prepared therewith is, however, at least hundreds of times the amount by weight of catalyst. The catalyst is, however, very active and is in that respect at least comparable with soluble organometallic compounds. Hydrated titanium dioxide is more active than e.g. tetrabutyl orthotitanate (TBT), particularly at the end of the reaction. As a result thereof, shorter conversion times than hitherto are possible.

The conversion is preferably carried out at a pressure which is higher than atmospheric. The pressure then is as a rule between 100 and 1000 k.Pa. The reaction temperature applied is, inter alia, dependent on the carboxylic acid to be converted, the activity of the catalyst, etc. As a rule this is between 120° and 240° C., preferably between 150° and 200° C. In order to cause the reaction to come to an end, it is necessary to remove water of reaction formed during the reaction, e.g. by regular ventilation of the autoclave (by blowing off and thereafter feeding in ammonia once more). The ammonia can also be recycled, with removal of the water of reaction formed, e.g. by one or more cooling steps.

It is possible according to the invention to use a starting material that consists of carboxylic acid and ammonia and the new catalyst, but this mixture can also first in part be partially converted into carbonamide, e.g. non-catalytically or with the aid of a not very active catalyst such as e.g. a silicate. Thereafter, in an efficient manner, a quicker further conversion into carbonamide can be effected by addition of active hydrated Group IV or Va metallic oxide and reacting further with ammonia.

This process in two or more steps lends itself admirably to being carried out continuously. The course of the reaction can be followed in a simple manner via the acid number. Carboxylic acid partially converted into amide that can be used as starting material mostly has an acid number of 5–50, preferably 10–30 mg KOH/g. According to the invention, products can be obtained having amide contents of 97 to 99% of the theoretically possible content and an acid number lower than 3 mg KOH/g.

The carboxylic acids converted according to the invention are those containing 10-44 carbon atoms. Preferably $C_{10}$-$C_{24}$ monocarboxylic acids which are saturated or or contain one or more double carbon-carbon bonds or polycarboxylic acids such as polymerized fatty acids can also be converted according to the invention, particularly $C_{36}$ to $C_{44}$ dimeric acids. Mostly, technical stearic acid, lauric acid, oleic acid, elaidic acid, erucic acid or linoleic acid is converted and possibly mixtures thereof. Preferably, mono-unsaturated carboxylic acids are converted.

The carbonamide thus prepared is light of colour and, as appears from the amide content, quite pure, while the nitrile content is low. This amide is used for various purposes, e.g. as slip agent for polyalkylene, as washing adjuvant, as textile adjuvant and as lubricant additive.

EXAMPLE 1

10 g titanium tetrachloride was carefully and dropwise poured into 400 g distilled water. As a result of hydrolysis a finely divided white precipitate formed. After warming to 50° C., 50 g ammonia (about 25% $NH_3$) was added under stirring. Thereafter stirring was continued for 5 minutes at 80° C. After filtration on a Büchner, the filtrate was washed with warm water and drawn off.

The moist (undried) precipitate, containing some 85% of water, was mixed into 2000 g technical oleic acid containing about 80% mono-unsaturated fatty acid. This mixture was drawn into a pressure vessel. Hereafter the vacuum was filled up with nitrogen. Under stirring, the mixture was heated to 180° C. under a nitrogen blanket. The water vapour formed, emanating from the moist catalyst, could escape through an opened valve in the autoclave. At 170° C. the vapour valve was closed and gaseous ammonia was fed in to 0.3 MPa and immediately thereafter the reaction was carried out under stirring under 0.38 Mpa. The pressure was released every 45 minutes in order to discharge the water of reaction.

After 6 hours of reaction the acid number was 13.5 mg KOH/g. After 12 hours of reaction the acid number was 2.4. After stirring in of 1% filter aid (Dicalite 478) the amide was filtered at 100° C. under 0.1 MPa excess pressure. The amide is a solid substance with a melting range of 67°-70° C. and colour of 6 Gardner. The amide content of the final product was 98%. The nitrile content was 0.6%.

COMPARATIVE EXAMPLE 1A 2000 g technical oleic acid was drawn into a pressure vessel. Nothing was added. The reaction conditions for the amidation with ammonia were the same as those of Example 1.

After 6 hours of reaction the acid number was 22 mg KOH/g. After 12 hours of reaction the acid number was 10.2 mg KOH/g, the amide content was 94% and the Gardner colour 6. If the amidation was continued in order to obtain a higher amide content it appeared that many hours of further reacting were needed and that in that case the colour deteriorated considerably.

EXAMPLE 2

In the same manner as described in Example 1, a titanium-containing catalyst was prepared from 10 g $TiCl_4$. The moist (undried) precipitate, containing about 80% of water, was mixed into 2000 g of 90% oleylamide at about 100° C. having acid number 18 and drawn into a pressure vessel.

N.B.: The 90% amide had been obtained by reaction, without catalyst, of oleic acid with ammonia under 0.4 MPa at 180° C.

The vacuum was filled up with nitrogen. The contents of the pressure vessel were heated to 180° C. under a nitrogen blanket. Between 100° and 150° C. the water vapour formed, emanating from the moist catalyst, could escape from the pressure vessel through an opened valve.

As soon as 150° C. had been reached, the amidation was started by the admission of 0.3 MPa gaseous ammonia. After 180° C. had been reached the reaction was carried out under 0.38 MPa ammonia pressure.

The pressure was released every 45 minutes for the reaction water formed to be removed in the form of water vapour. After 7.5 hours of reaction the acid number of the amide dropped to 2.4. After stirring in of 1% filter aid (Dicalite 478), the amide was filtered at 100° C. under 0.1 MPa $N_2$ excess pressure. The amide content of the final product was 98%. The nitrile content was 0.4%.

Samples taken after 1.5, 3 and 7.5 hours of reaction were filtered at 90° C. The titanium contents of these filtered samples were smaller than 15 mg/kg. A part of the sample after 1.5 hours of reaction was also filtered at 180° C. (i.e. at reaction temperature). The filtered amide likewise contained less than 15 mg Ti per kg. Because of the amount of catalyst which had been added to the 90% amide, 1260 mg titanium per kg amide was present. This amount of titanium was practically all present in an undissolved form.

COMPARATIVE EXAMPLE 2A 2000 g 90% oleylamide having acid number 18 (the same starting material as in Example 2) was drawn into a pressure vessel. Nothing was added. The reaction conditions for the amidation with ammonia were for the rest the same as those of Example 2. After 7.5 hours of reaction the acid number was 8 mg KOH/g. After 13 hours of reaction at 180° C. under 0.38 MPa the acid number of the reaction mixture dropped to 6.0 mg KOH/g.

COMPARATIVE EXAMPLE 2B 4.2 g titanium dioxide Kronos R 1053 (rutile form), water content 0.16% determined by Carl Fischer method, was stirred into 2000 g molten oleylamide having acid number 18 (the same starting material as in Example 2). This mixture was drawn into a pressure vessel and amidated in the same manner as described in Example 2. After 7.5 hours of reaction the acid number had dropped to 7.5 mg KOH/g.

COMPARATIVE EXAMPLE 2C 4.2 g titanium dioxide Kronos AD (anatase form), water content 0.35% determined by Carl Fischer method, was stirred into 2000 g molten oleylamide having acid number 18 (the same starting material as in Example 2). This mixture was amided in the same manner as described in Example 2. After 7.5 hours of reaction the acid number had dropped to 7.6 mg KOH/g.

EXAMPLE 3

In the same manner as described in Example 1, a titanium-containing catalyst was prepared from 10 g $TiCl_4$. The filter cake obtained was, however, dried for 15 hours at 110° C. under vacuum. As determined by the Karl Fischer method, the water content was 40%. The dried precipitate was stirred into 2000 g oleylamide having acid number 18 (the same starting material as in Example 2) and drawn into a pressure vessel. Hereafter the vacuum in the pressure vessel was filled up with nitrogen. Subsequently the mixture was reacted with ammonia at 180° C. under 0.38 MPa as described in Example 2. After 7.5 hours of reaction the acid number had dropped to 6.7 mg KOH/g.

EXAMPLE 4

The filter cake of 1825 g unfiltered reaction product of Example 2 was stirred into 1800 g molten oleylamide having acid number 18 (as in Example 2) at about 100° C. This mixture was drawn into a pressure vessel. Hereafter the vacuum was filled up with nitrogen. The contents of the pressure vessel were heated to 180° C. under a nitrogen blanket.

Ammonia was first admitted at 150° C. into the reactor to 0.3 MPa. After 180° C. had been reached, reaction with ammonia was carried out under 0.38 MPa. The pressure was released every 45 minutes. After 7.5 hours of reaction the acid number of the reaction mixture had dropped to 2.7. The amide was filtered at 100° C. under 0.1 MPa nitrogen excess pressure. The amide content in the final product was 98%. The nitrile content was 0.8%.

COMPARATIVE EXAMPLE 4A 20 g Dicalite 478 was stirred into 2000 g molten oleylamide having acid number 18 (the same starting material as in Example 2). This mixture was drawn into a pressure vessel. Hereafter the vacuum was filled up with nitrogen. The contents of the pressure vessel were heated to 180° C. under a nitrogen blanket. Ammonia was already admitted at 150° C. into the reactor to 0.3 MPa. After 180° C. had been reached, reaction with ammonia was carried out under 0.38 MPa. The pressure was released every 45 minutes. After 7.5 hours of reaction the acid number of the reaction product had dropped to 6.8 mg KOH/g.

EXAMPLE 5

In a manner similar to that described in Example 1, a titanium-containing catalyst was prepared from 2 g TiCl$_4$. The moist precipitate, containing about 90% of water, was mixed into 2000 g oleylamide having acid number 18 (the same starting material as in Example 2). This mixture was drawn into a pressure vessel. The vacuum was filled up with nitrogen. The contents of the pressure vessel were heated to 180° C. under injection of nitrogen.

Between 100° and 150° C. the water vapour formed, emanating from the moist catalyst, could escape from the pressure vessel through an opened valve. The amidation was carried out in the same way as in Example 2. After 7.5 hours of reaction the acid number had dropped to 6.2 mg KOH/g (the amount of catalyst employed was below 0.1%).

EXAMPLE 6

20 g filter aid (Dicalite 478) was dispersed into 800 g distilled water. 10.2 g tin tetrachloride was slowly added to this dispersion under stirring. Subsequently the dispersion was heated to 90° C. At this temperature 50 g ammonia was poured in under stirring and the stirring was continued a further 5 minutes.

Hereafter the stirring was interuppted for 5-10 minutes in order to allow the precipitate to settle somewhat. The upper layer was poured off on a Büchner funnel and subsequently the settled precipitate was filtered off on the same Büchner and washed a number of times with warm water.

The moist filter cake was mixed into 2000 g 90% oleylamide of about 100° C. and acid number 18 mg KOH/g (cf. Example 2). The mixture was drawn into a pressure vessel, the vacuum filled up with nitrogen and the contents heated to 180° C. under a nitrogen blanket. Between 100° and 150° C. the water vapour formed, emanating from the catalyst, could escape through the opened valve.

The amidation was already started as soon as 150° C. had been reached by admission of 0.3 MPa gaseous ammonia. After 180° C. had been reached the reaction was carried out under 0.38 MPa ammonia pressure. The pressure was released every 45 minutes for the water of reaction formed to be removed. After a reaction time of 7.5 hours the amidation was stopped and the mixture was filtered at 100° C. under 0.1 MPa nitrogen excess pressure. The acid number of the final product was 4.3 mg KOH/g.

EXAMPLE 7

10 g zirconium tetrachloride was carefully dissolved in 600 g distilled water of 25° C. The solution was warmed to about 50° C. Thereafter precipitation was effected by addition of 50 g ammonia (25% NH$_3$). Hereafter the mixture was stirred for one hour more. Subsequently the filtration was carried out on a Büchner and the filtrate was washed with water. The moist filter cake, containing about 85% of water, was mixed into 2000 g 90% oleylamide at about 100° C. and acid number 18 mg KOH/g (compare Example 2). This mixture was drawn into a pressure vessel. Subsequently the vacuum was filled up with nitrogen. The contents of the pressure vessel were heated to 180° C. under a nitrogen blanket. Between 100° and 150° C. the water vapour formed could escape through an opened valve. The amidation was already started as soon as 150° C. had been reached by admission of 0.3 MPa gaseous ammonia. The pressure was released every 45 minutes for the water of reaction formed to be removed. After a reaction time of 7.5 hours the amidation was stopped. At 100° C. 20 g Dicalite 4178 was stirred in and subsequently, at 100° C. under 0.1 MPa pressure, filtration was carried out. The acid number of the final product was 2.2 mg KOH/g.

EXAMPLE 8

The filter cake of 1520 g reaction product of Example 7 was stirred into 1500 g molten oleylamide at about 100° C. having acid number 18 (as in Example 2). This mixture was drawn into a pressure vessel. Hereafter work proceeded as in Example 4. After 7.5 hours of reaction the acid number of the reaction mixture had dropped to 1.8 mg KOH/g. The amide content was 98%.

EXAMPLE 9

This example relates to the conversion of C$_{36}$-dimerized fatty acids (Monomer:Dimer:Trimer=1:95:4, a.v. 195, Gardner colour 5) into amides.

The reaction was carried out in an open vessel at atmospheric pressure and NH$_3$ gas was passed through at a rate of 160 liters (STP) per kg of dimerized fatty acids.

Two runs were made, viz, one without catalyst and the second with 0.5% (calculated as dry matter) of titanium dioxide added in the form of an aqueous dispersion with a dry matter content of 17.5%. The catalyst was added after 4 hours reaction without catalyst.

Heating to 180° C. and passing through ammonia gas were continued for 15 hours and samples were drawn each hour and acid values determined in order to gain an insight into amide formation (Theoretical conversion percentage is (195−a.v.)/1.95). The results are tabulated below.

| Time of reaction (hours) | Acid value (no catalyst) | | Acid value (with catalyst) |
| --- | --- | --- | --- |
| 1 | — | | — |
| 2 | 73 | | 75 |
| 3 | 56 | | 57 |
| 4 | 45 | catalyst | 46 |
| 5 | 35.6 | added → | 36.7 |
| 6 | 32.6 | | 27.1 |
| 7 | 28.7 | | 20.6 |
| 8 | 25.7 | | 15.2 |
| 9 | 23.3 | | 10.1 |
| 10 | 21.3 | | 7.7 |
| 11 | 19.7 | | 5.4 |
| 12 | 18.1 | | 3.7 |
| 13 | 17.0 | | 2.5 |
| 14 | 16.2 | | 1.6 |
| 15 | 15.1 | | 1.2 |

We claim:

1. A process for the preparation of carbonamides by conversion of carboxylic acids containing 10-44 carbon atoms with ammonia in the presence of a metallic compound as a catalyst, characterized in that the carboxylic acid is converted with ammonia in the presence of a solid catalyst consisting essentially of an insoluble hydrated dioxide of an element of Group IVa, IVb or Va of the Periodic Table which reduces the conversion time and which is removable from the reaction mixture by filtration.

2. A process according to claim 1, characterized in that the metal is an element of Group IVa.

3. A process according to claim 1, characterized in that the hydrated oxide predominantly consists of titanium and/or zirconium dioxide.

4. A process according to claim 1, characterized in that the preparation is carried out with hydrated dioxide containing from 4 to 95, percent by water.

5. A process according to claim 1, characterized in that the amount of hydrated metallic compound (calculated as metallic oxide on the reaction mixture) is between 0.05 and 10%, preferably between 0.15 and 1.5% by weight.

6. A process according to claim 1, characterized in that the reaction is carried out at a pressure higher than atmospheric pressure.

7. A process according to claim 1, characterized in that a reaction mixture consisting of carboxylic acid that has been partially converted into carbonamide is used as starting material together with ammonia.

8. A process according to claim 1, in which the reaction is carried out discontinuously, the catalyst being re-used.

9. A process according to claim 1, characterized in that the reaction is carried out continuously.

10. A process according to claim 4 wherein the hydrated dioxide contains from 70 to 90% of water.

* * * * *